(12) United States Patent
Takai et al.

(10) Patent No.: US 7,790,936 B2
(45) Date of Patent: Sep. 7, 2010

(54) PROCESS FOR PREPARING ALKYLATED AROMATIC COMPOUND

(75) Inventors: Toshihiro Takai, Nishinomiya (JP); Michiaki Umeno, Chiba (JP); Shinobu Aoki, Ichihara (JP); Terunori Fujita, Yokohama (JP); Tsuneyuki Ohkubo, Ichihara (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 12/526,542

(22) PCT Filed: Feb. 12, 2008

(86) PCT No.: PCT/JP2008/052225

§ 371 (c)(1),
(2), (4) Date: Aug. 10, 2009

(87) PCT Pub. No.: WO2008/102664

PCT Pub. Date: Aug. 28, 2008

(65) Prior Publication Data

US 2010/0022805 A1 Jan. 28, 2010

(30) Foreign Application Priority Data

Feb. 23, 2007 (JP) ............................ 2007-044363
Jun. 1, 2007 (JP) ............................ 2007-146445

(51) Int. Cl.
*C07C 33/18* (2006.01)
*C07C 39/00* (2006.01)
*C07C 15/067* (2006.01)
*C07C 2/68* (2006.01)

(52) U.S. Cl. ...................... 568/715; 568/716; 585/446; 585/467

(58) Field of Classification Search .................. 568/715, 568/716
See application file for complete search history.

(56) References Cited

U.S. PATENT DOCUMENTS 4,992,606 A 2/1991 Kushnerick et al.

| | | |
|---|---|---|
| 5,453,554 A | 9/1995 | Cheng et al. |
| 7,524,788 B2 | 4/2009 | Girotti et al. |
| 2004/0162448 A1 | 8/2004 | Yang et al. |
| 2005/0075239 A1* | 4/2005 | Girotti et al. .................. 502/64 |

FOREIGN PATENT DOCUMENTS

| | | |
|---|---|---|
| EP | 1 069 099 | 1/2001 |
| JP | 57091972 | 6/1982 |
| JP | 2174737 | 7/1990 |
| JP | 2231442 | 9/1990 |
| JP | 3291248 | 12/1991 |
| JP | 11035497 | 2/1999 |
| JP | 2003513116 | 4/2003 |
| JP | 2003523985 | 8/2003 |
| JP | 2005513116 | 5/2005 |

OTHER PUBLICATIONS

International Search Report for PCT/JP2008/052225 dated Mar. 11, 2008.
Sigmund M. Csicsery, "Shape-selective catalysis in zeolites", Zeolites, Jul. 1984, vol. 4, No. 3, pp. 202-213.
M.F. Bentham et al., "Development and Commercialization of Solid Acid Catalysts", Erdol Erdgas Kohle, Feb. 1997, 113. Jahrgang, Heft 2, pp. 84-88.
A. Corma et al., "Alkylation of Benzene with Short-Chain Olefins over MCM-22 Zeolite: Catalytic Behaviour and Kinetic Mechanism", Journal of Catalysis, May 15, 2000, vol. 192, No. 1, pp. 163-173.
Extended European Search Report for EP 08 71 1089 mailed on Feb. 18, 2010.
Barman, et al. Kinetics of Reductive Isopropylation of Benzene with Acetone over Nano-Copper Chromite-Loaded H-Mordenite, Industrial & Engineering Chemistry Research, American Chemical Society, US, vol. 45, No. 10, Apr. 14, 2006, pp. 3481-3487, XP002552820.

* cited by examiner

*Primary Examiner*—Sikarl A Witherspoon
(74) *Attorney, Agent, or Firm*—Turocy & Watson, LLP

(57) ABSTRACT

The present invention provides a process in which a ketone is directly reacted with an aromatic compound in a single reaction step to obtain the corresponding alkylated aromatic compound in a higher yield. By reacting an aromatic compound with a ketone and hydrogen in the presence of a solid acid substance and a catalyst composition containing Cu and Zn in a ratio of Zn to Cu ranging from 0.70 to 1.60 (atomic ratio), the corresponding alkylated aromatic compound is prepared.

7 Claims, No Drawings

US 7,790,936 B2

PROCESS FOR PREPARING ALKYLATED AROMATIC COMPOUND

TECHNICAL FIELD

The present invention relates to a process for preparing the corresponding alkylated aromatic compound by reacting an aromatic compound with a ketone and hydrogen. More particularly, the present invention relates to a process in which cumene is prepared in a single reaction step in a high yield using a solid acid substance and a catalyst composition containing Cu and Zn as catalysts and using acetone, benzene and hydrogen as starting materials.

BACKGROUND ART

A process for preparing cumene by reacting benzene with propylene, a process for preparing cumene hydroperoxide by oxidizing cumene and a process for preparing phenol and acetone by acid decomposing cumene hydroperoxide are publicly known, and a process combining these reactions is a phenol preparation process generally called a cumene process. At present, this cumene process is the mainstream of the phenol preparation process.

This cumene process is characterized in that acetone is simultaneously produced, and this is advantageous when acetone is needed at the same time, but this is economically disadvantageous when acetone is in excess. Then, in order to lead a difference in price between an olefin as a raw material and a ketone produced simultaneously to an advantageous direction, there has been proposed, for example, a process in which secondary butylbenzene obtained from n-butene and benzene is oxidized and acid decomposed to obtain phenol and methyl ethyl ketone at the same time (see patent document 1 and patent document 2). In this process, however, the selectivity of the aimed secondary butylbenzene hydroperoxide obtained by the oxidation of secondary butylbenzene is only about 80%, and in addition, not less than 15% of acetophenone is formed as a side product. Therefore, this process is inferior, as the phenol preparation process, to the cumene process in yield.

Further, there has been also proposed a process in which cyclohexylbenzene obtained from cyclohexene and benzene is oxidized and acid decomposed to obtain phenol and cyclohexanone. In this process, phenol is obtained by dehydrogenating the resulting cyclohexanone, so that formation of a ketone as a side product can be avoided formally. In this process, however, the yield of the aimed cyclohexylbenzene hydroperoxide obtained by the oxidation reaction of cyclobenzene is much lower, and its industrial value is low.

Accordingly, in order to avoid problems of propylene that is a raw material and acetone that is produced simultaneously while maintaining an advantage of the cumene process wherein the yields of oxidation and acid decomposition are highest, there have been proposed processes in which acetone simultaneously produced is recycled as a raw material of the cumene process by the use of various methods. Acetone can be readily converted into isopropanol by hydrogenation, so that a process in which isopropanol is further subjected to dehydration reaction to convert it into propylene, then the propylene is reacted with benzene to obtain cumene and the propylene is recycled as a raw material of the cumene process has been proposed (see patent document 3). In this process, however, there is a problem that the two steps, i.e., a hydrogenation step and a dehydration step are further required.

Accordingly, a process in which isopropanol obtained by hydrogenation of acetone is directly reacted with benzene to obtain cumene has been proposed (see patent document 4 and patent document 5). Especially in a patent document 6, there has been described a process in which acetone simultaneously produced is converted into isopropanol, then the isopropanol is reacted with benzene to obtain cumene, and using the cumene, phenol is prepared. In this process, however, a hydrogenation step is required in addition to the original cumene process.

In contrast with the above, as a process in which acetone simultaneously produced is recycled without increasing the number of steps of the conventional cumene process, that is, a process in which acetone is directly reacted with benzene, there has been disclosed a process for preparing an alkylated aromatic compound, comprising reacting an aromatic compound with a ketone and hydrogen in the presence of a solid acid substance and a catalyst composition containing copper (see patent document 7). As the Cu-based reduction catalyst in the examples, however, a Cu-based catalyst containing, as a second component, Cr or Al and a slight amount of Zn is only disclosed. Further, it is described that zeolite can be used as the solid acid substance, but β-zeolite is only disclosed in the examples. The present inventors used the copper-chromium catalyst in the examples and chabazite as the solid acid substance, but cumene was not formed virtually. Moreover, among zeolites, there is one having much smaller pore diameters as compared with molecular diameters of benzene or cumene (non-patent document 1), so that it is readily presumed that the reaction itself is impossible with such a catalyst. As described above, formation of cumene is not satisfactory in the case of a solid acid substance different from the examples. As a result of actual inspection by the present inventors, a hydrocarbon derived from acetone is formed as a side product by any of the above catalysts, and the processes proved to be unsatisfactory as industrial production processes. That is to say, the selectivity of cumene is extremely low in the case of the conventional catalysts, and the industrial level has not been reached at all.

Patent document 1: Japanese Patent Laid-Open Publication No. 91972/1982
Patent document 2: U.S. Pre Grant Patent No. 0162448/2004
Patent document 3: Japanese Patent Laid-Open Publication No. 174737/1990
Patent document 4: Japanese Patent Laid-Open Publication No. 231442/1990
Patent document 5: Japanese Patent Laid-Open Publication No. 35497/1999
Patent document 6: National Publication of International Patent No. 523985/2003
Patent document 7: National Publication of International Patent No. 513116/2005
Non-patent document 1: ZEOLITES, Vol. 4, pp. 202-213, 1984

DISCLOSURE OF THE INVENTION

Problem to be Solved by the Invention

Accordingly, in order to directly react acetone with benzene to obtain cumene, development of a novel catalyst system of higher activity and higher selectivity has been desired.

Means to Solve the Problem

The present inventors have earnestly studied in order to solve the above problems, and as a result, they have found that by using, as catalysts, a solid acid substance and a catalyst composition containing specific metals in a specific quantity ratio and by using a ketone such as acetone, an aromatic compound such as benzene and hydrogen as starting materials, the corresponding alkylated aromatic compound such as cumene is obtained in a single reaction step in a high yield. Further, they have found that formation of a hydrocarbon as a side product is extremely little.

That is to say, the present invention is a process for preparing the corresponding alkylated aromatic compound, comprising reacting an aromatic compound with a ketone and hydrogen in the presence of a solid acid substance and a catalyst composition containing Cu and Zn in a ratio of Zn to Cu ranging from 0.70 to 1.60 (atomic ratio). The present invention is also a process for preparing phenol, comprising the following steps of:

(a) a step of oxidizing cumene to convert it into cumene hydroperoxide, (b) a step of acid decomposing the cumene hydroperoxide to synthesize phenol and acetone, (c) a step of reacting the acetone formed in the step (b) with benzene to synthesize cumene, and (d) a step of recycling the cumene obtained in the step (c) to the step (a), wherein the step (c) is carried out in accordance with the aforesaid process for preparing the alkylated aromatic compound.

EFFECT OF THE INVENTION

According to the present invention, using a ketone such as acetone, an aromatic compound such as benzene and hydrogen as starting materials, the corresponding alkylated aromatic compound such as cumene can be obtained in a single reaction step in a higher yield. Therefore, in a process for preparing phenol by the cumene process, acetone that is simultaneously produced can be reused more efficiently. Moreover, the process of the present invention is an epoch-making technique such that there is no difference in quality between the resulting cumene and cumene obtained from propylene or isopropanol and benzene, so that phenol can be prepared extremely advantageously from the viewpoints of process and economy.

BEST MODE FOR CARRYING OUT THE INVENTION

In the reaction of the present invention, a solid acid substance and a catalyst composition containing Cu and Zn in a ratio of Zn to Cu ranging from 0.70 to 1.60 (atomic ratio) are used. In the present invention, the above two components have only to be used, and the method of utilizing them is not specifically restricted. That is, acid catalyst component that is the solid acid substance and the catalyst composition component containing at least Cu and Zn may be physically mixed on a catalyst particle level of centimeter size, or after they are finely divided and mixed, the resulting mixture may be molded into catalyst particles of centimeter size, or the catalyst composition component containing metals may be supported on the acid catalyst component that is used as a carrier, or contrary to this, the acid catalyst component may be supported on the catalyst composition component containing metals that is used as a carrier.

In the present invention, it is important from the viewpoints of activity and selectivity that the metal quantities in the catalyst composition containing Cu and Zn are such that the atomic ratio of Zn to Cu is in the range of 0.70 to 1.60.

If the atomic ratio is less than 0.70, the activity and the selectivity are insufficient, and if the atomic ratio exceeds 1.60, the activity is insufficient. The atomic ratio is preferably in the range of 0.80 to 1.50. The content of Cu is in the range of preferably 5 to 55%, more preferably 10 to 50%. If the amount of Cu that is an active species is too small, a large catalytic amount becomes necessary, and the reactor also becomes excessive, so that the cost of equipment is high, resulting in poor economy. If the content of Cu is too large, a proper atomic ratio of Zn to Cu cannot be maintained.

With regard to the conditions other than the quantity ratio of Zn to Cu, methods and conditions disclosed in the patent document 7 can be utilized in the process of the present invention. For example, with regard to a process for preparing the catalyst composition containing Cu and Zn, other components, utilization method, specific examples of the solid acid substances, use method, etc., methods, conditions, etc. disclosed in the above document can be utilized.

For example, the catalyst composition containing Cu and Zn may contain other metals within limits not detrimental to the object of the present invention, and examples of the other metals include Al and Fe. In the case where the catalyst composition contains these metals, the quantity ratio of them to Cu is not more than 10% by weight.

In the catalyst composition containing Cu and Zn in the present invention, Cu and Zn may have any structure, but it is preferable that Cu and Zn are each contained in the form of a metal oxide. When other metals are contained, those metals also are each preferably in the form of an oxide. Although the process for preparing the catalyst composition is not specifically restricted, the catalyst composition can be prepared by, for example, a wet process. Examples of the wet processes include an impregnation process and a co-precipitation process. Of these, the co-precipitation process is preferable from the viewpoint that high activity is obtained.

As the catalyst preparation process using the co-precipitation process, there can be specifically mentioned, for example, a process comprising bringing an aqueous solution that is a mixture of aqueous solutions of acid salts of metallic elements such as copper, zinc and iron into contact with an aqueous solution of a basic compound to give a precipitate, washing/recovering the precipitate, drying the recovered precipitate and then calcining the dried product. The acid salts of metallic elements are not specifically restricted provided that oxides of metallic elements are given by drying/calcining a precipitate obtained by the reaction of the acid salts with a basic compound. Examples of such acid salts include nitrate, sulfate and hydrochloride. Examples of the basic compounds which are brought into contact with the acid salts of metallic elements include carbonates of alkali metals or alkaline earth metals and bicarbonates thereof.

The method to bring the aqueous solutions of acid salts of metallic elements into contact with the aqueous solution of a basic compound is not specifically restricted provided that pH of an aqueous solution obtained by the contact of them can be controlled to be in the range of 6 to 9. Examples of such methods include a method of mixing the aqueous solution of a basic compound with the aqueous solutions of acid salts of metallic elements at the same time, a method of adding an aqueous solution that is a mixture of the aqueous solutions of acid salts of metallic elements to the aqueous solution of a basic compound, and a method of adding the aqueous solution of a basic compound to a solution that is a mixture of the aqueous solutions of acid salts of metallic elements. The temperature to bring the aqueous solutions of acid salts of metallic elements into contact with the aqueous solution of a basic compound is not specifically restricted provided that the temperature is in the range of about 10 to about 80° C.

The precipitate obtained by reacting the acid salts of metallic elements with the basic compound is washed with water at a temperature of usually room temperature to 50° C. and then dried by air or in an inert gas atmosphere at a temperature of about 100 to 160° C. After drying, the dried product is calcined, whereby the catalyst of the present invention can be obtained. The calcination can be carried out at a temperature of about 200° C. to 470° C. The calcination temperature is preferably not higher than 450° C. A calcination temperature of not lower than 300° C. is preferable because decomposition of the precipitate is sufficiently carried out. The calcination is usually carried out in the presence of air or an inert gas.

The catalyst after calcination can be used for the reaction as it is, but it is also possible that the catalyst after calcination is treated with a reducing gas such as hydrogen or carbon monoxide in a liquid phase or a gas phase and then used for the reaction.

The catalyst composition containing Cu and Zn is subjected to tablet-making molding or extrusion molding and then used for the reaction, or it can be supported on a ceramic carrier such as mullite or cordierite, a silica cloth, a spongy metal sintered porous plate or the like to form a honeycomb catalyst and then used for the reaction.

The catalyst composition containing Cu and Zn is sometimes enhanced in activity or selectivity by adding metal salts, such as $PbSO_4$, $FeCl_2$ and $SnCl_2$, alkali metals such as K and Na or alkali metal salts, $BaSO_4$, or the like, and therefore, they may be added when necessary.

The shape of the catalyst composition containing Cu and Zn is not specifically restricted, and any of spherical, cylindrical, extruded and crushed shapes is available. The size of its particle is in the range of 0.01 mm to 100 mm and is selected according to the size of the reactor.

The solid acid substance for use in the present invention is a catalyst having a function as an acid and has only to be a substance that is generally called a solid acid. As such a solid acid substance, zeolite, silica alumina, alumina, sulfur ion-supported zirconia, $WO_3$-supported zirconia or the like is employable.

In particular, a zeolite compound that is an inorganic crystalline porous compound composed of silicon and aluminum is a preferred catalyst from the viewpoints of heat resistance and selectivity of the desired cumene. As the zeolite compound, a zeolite compound having a 10- to 16-membered oxygen ring is employable.

Examples of the zeolite compounds having a 10- to 16-membered oxygen ring include ferrierite, heulandite, ZSM-5, ZSM-11, ZSM-12, NU-87, Theta-1, weinebeneite, X type, Y type, USY type, mordenite type, dealuminated mordenite type, β type, MCM-22 type, MCM-36, MCM-56 type, gmelinite, offretite, cloverite, VPI-5 and UTD-1.

Of the zeolite compounds, those having pores of similar diameters to the molecular diameters of cumene are preferable, and a preferred structure is a pore constituted by 12 oxygen atoms, that is, a pore of a 12-membered oxygen ring. Examples of the zeolite compounds having a structure of a 12-membered oxygen ring include Y type, USY type, mordenite type, dealuminated mordenite type, β type, MCM-22 type, MCM-56 type and ZSM-12. An example of the zeolite compound having a 10-membered oxygen ring structure includes ZSM-5.

From literature on alkylation of benzene by propylene that is an analogous reaction (e.g., U.S. Pat. No. 4,992,606, U.S. Pat. No. 5,453,554, Erdoel Erdgas Khole, 113, 84, 1997), it is presumed that β type, MCM-22 type and MCM-56 type are particularly preferred structures. With regard to β type and MCM-22, it is described in literature that MCM-22 is a little superior to β type in catalytic activity and selectivity of cumene (e.g., U.S. Pat. No. 5,453,554), but it is described in other literature that there is little difference between them in performance (e.g., Journal of Catalysis, 192, 163-173, 2000), so that a difference in superiority or inferiority is not clear. In the prior techniques, there is no description on the formation of a hydrocarbon that is detrimental to economical efficiency, and it is astonishing that the reaction to produce propane by further hydrogenating propanol that is produced with a Cu catalyst in the presence of acetone is inhibited depending upon the type of the acid catalyst. Further, it cannot be expected at all that the inhibition effects of MCM-22 and MCM-56 are greater. The compositional ratio of silicon to aluminum in these zeolite compounds is in the range of 2/1 to 200/1, and particularly from the viewpoints of activity and heat stability, it is in the range of preferably 5/1 to 100/1.

Further, so-called isomorphous substituted zeolite wherein metals other than aluminum, such as Ga, Ti, Fe, Mn and B, are substituted for aluminum atoms contained in the zeolite skeleton is also employable.

The shape of the solid acid substance is not specifically restricted, and any of spherical, cylindrical, extruded and crushed shapes is available. The size of its particle is in the range of 0.01 mm to 100 mm and is selected according to the size of the reactor.

It is also possible that the catalyst composition containing Cu and Zn is supported on an acid catalyst as a carrier that is the solid acid substance. Specifically, the catalyst composition can be supported by a method in which the acid catalyst is impregnated with an aqueous solution of nitrate of the metals and then calcined, a method in which these metals are bonded to organic molecules called ligands to prepare complexes in order to make the metals soluble in an organic solvent and the acid catalyst is impregnated with an organic solvent and then calcined, a method of vapor deposition because some complexes are vaporized under vacuum, etc. Moreover, also adoptable is a coprecipitation process in which synthesis of a carrier and supporting of metals are carried out simultaneously by allowing a metal salt that becomes the catalyst composition containing Cu and Zn to coexist when an acid catalyst is obtained from the corresponding metal salt.

The ratio of the catalyst composition containing Cu and Zn to the solid acid substance is in the range of usually 0.001 to 10, preferably 0.01 to 2, in terms of mass ratio of Cu to the solid acid substance.

When the present invention is carried out, it is desirable to dehydrate the solid acid substance and the catalyst composition containing Cu and Zn by a publicly known method. In the case of a fixed bed reaction system, the catalyst and the cocatalyst are charged in a reactor and maintained at a temperature of not lower than 300° C. for not shorter than 10 minutes with passing an inert gas such as nitrogen or helium through the reactor. In order to allow the catalyst composition containing Cu and Zn to exhibit activity, treatment in a stream of hydrogen can be carried out after the dehydration treatment.

Examples of methods to charge proper species of catalysts in order correspondingly to the stage of the reaction include (1) a method in which the solid acid substance and the catalyst composition containing the metals are mixed and the mixture is charged, (2) a method in which the catalyst composition containing the metals and the solid acid substance are charged so as to form a layer composed of the catalyst composition containing the metals (on the upstream side) and a layer composed of the solid acid substance (on the downstream side), (3) a method in which the solid acid substance on which the catalyst composition containing the metals has been supported is charged, (4) a method in which the catalyst composition containing the metals and the solid acid substance are charged so as to form a layer composed of the catalyst composition containing the metals (on the upstream side) and a layer composed of the solid acid substance and the catalyst composition containing the metals (on the downstream side), (5) a method in which the catalyst composition containing the metals and the solid acid substance are charged so as to form a layer composed of the catalyst composition containing the metals (on the upstream side) and a layer composed of the solid acid substance on which the catalyst composition containing the metals has been supported (on the downstream side), (6) a method in which the catalyst composition containing the metals and the solid acid substance are charged so as to form a layer composed of the solid acid substance and the catalyst composition containing the metals (on the upstream side) and a layer composed of the solid acid substance (on the downstream side), and (7) a method in which the catalyst composition containing the metals and the solid acid substance are charged so as to form a layer composed of the solid acid substance on which the catalyst composition containing the metals has been supported (on the upstream side) and a layer composed of the solid acid substance (on the downstream side). The "upstream side" indicates the entrance side of the reactor, that is, the layer through which the raw materials pass in the first half of the reaction, and the "downstream side" indicates the exit side of the reactor, that is, the layer through which the raw materials pass in the latter half of the reaction.

In the present invention, the aromatic compound is, for example, a compound of 6 to 20 carbon atoms, and examples of such compounds include benzene homologues, such as benzene, toluene and xylene, their substituent derivatives, naphthalene homologues, such as naphthalene and methylnaphthalene, and their substituent derivatives. The ketone is, for example, a compound of 3 to 20 carbon atoms, and a symmetric one or an asymmetric one can be used. The group bonded to carbonyl group is, for example, an alkyl group or an aryl group. Specific examples of the ketones include acetone, methyl ethyl ketone and acetophenone.

It is industrially most important that acetone and benzene are reacted as a combination of the ketone and the aromatic compound to prepare cumene.

The reaction of the aromatic compound with the ketone in the present invention is characterized in that it is carried out in the presence of hydrogen. The "hydrogen" referred to herein may be a molecular hydrogen gas or may be a hydrocarbon such as cyclohexane that generates hydrogen under the reaction conditions. In the case where acetone is reacted with benzene, hydrogen has only to be present in an equimolar quantity or more with acetone in principle from the viewpoints of separation and recovery of cumene, and a preferred quantity is in the range of 1 to 10 times, preferably 1 to 15 times, the molar quantity of acetone. When it is desired to reduce the conversion of acetone to not more than 100% for the purpose of separating and recovering acetone, the quantity of hydrogen used is decreased to less than an equimolar quantity of acetone, whereby it can be coped with. Hydrogen fed to the reaction of the present invention reacts with an oxygen atom of acetone to produce water, and this water goes out from the exit of the reactor. Therefore, hydrogen in more than the equivalent quantity with acetone is not substantially consumed so long as an unfavorable side reaction does not proceed.

In the case where a hydrogen gas is introduced to the reaction, the gas is usually fed continuously. However, feeding of a hydrogen gas is not limited to this way, and there may be carried out such intermittent feeding that after addition of a hydrogen gas at the beginning of the reaction, feeding is ceased during the reaction, and after a certain period of time, a hydrogen gas is fed again, or in the case of liquid phase reaction, a hydrogen gas may be fed after it is dissolved in a solvent. In the recycle process, a hydrogen gas recovered from the top of a column may be fed together with a light boiling fraction. Although the pressure of hydrogen introduced is generally equal to that of the reactor, it may be appropriately changed according to the way of feeding of hydrogen.

When the reaction is carried out, its conditions are not specifically restricted, and usual methods and reaction conditions hitherto publicly known can be adopted as they are. Various modifications are also known, and they are also applicable. For example, the following conditions and methods are adoptable.

Contact of a mixture of acetone and benzene that are reaction raw materials with a hydrogen gas may be carried out by any of gas-liquid countercurrent and gas-liquid cocurrent, and the directions of the liquid and the gas may be any of downward flow of liquid-upward flow of gas, upward flow of liquid-downward flow of gas, upward flow of liquid and gas, and downward flow of liquid and gas.

Although the reaction temperature is not specifically restricted either, it is in the range of preferably 50 to 300° C., more preferably 60 to 200° C. In usual, the working pressure is in the range of preferably 0.01 to 100 MPa, more preferably 0.05 to 50 MPa. When the present invention is carried out, the catalytic amount used is not specifically restricted, but for example, in the case where the reaction is carried out using a fixed bed flow device, the catalytic amount is in the range of preferably 0.1 to 200/hr, more preferably 0.2 to 1000/hr, in terms of a value obtained by dividing an amount (weight) of the raw material fed per hour by the weight of the catalyst, that is, WHSV. The pressure is a gauge pressure unless otherwise noted.

When the present invention is carried out, it is also possible that a solvent or a gas that is inert to the catalyst and the reaction reagent is added to the reaction system and the reaction is performed in a dilute state.

The present invention can be carried out by any of a batch process, a semi-batch process and a continuous flow process. The present invention can be carried out in any of a liquid phase, a gas phase and a gas-liquid mixed phase. As the catalyst charge systems, various systems, such as a fixed bed, a fluidized bed, a suspension bed and a plate fixed bed, are adopted, and the present invention may be carried out in any of these systems.

In the case where the catalytic activity decreases after the lapse of a certain period of time, the activity of the catalyst can be recovered by performing regeneration through a publicly known method.

In order to maintain the volume of production of cumene, Merry-go-round method in which two or three reactors are arranged in parallel, and while regeneration is performed by one reactor, the reaction is carried out by the residual one or two reactors may be adopted. In the case where three reactors are used, two of them may be connected in series to reduce variation of production. In the case where the present invention is carried out in a fluidized bed flow reaction system or a moving bed reaction system, it is possible to maintain a given activity by drawing a part or all of the catalyst out of the reactor continuously or intermittently and replenishing the corresponding amount.

In the present invention, through the above process, cumene can be directly obtained from acetone that is a side product of the preparation of phenol. The thus obtained cumene is employable as a raw material for preparing phenol and acetone, and is applicable to such a process comprising the aforesaid step (a) to step (d) wherein cumene is oxidized and then decomposed. Further, various modifications can be provided without any problem.

EXAMPLES

Example 1

Preparation of Catalyst

In 700 ml of pure water, 30.37 g of copper nitrate trihydrate [$Cu(NO_3)_2 \cdot 3H_2O$], 32.90 g of zinc nitrate hexahydrate [$Zn(NO_3)_2 \cdot 6H_2O$] and 7.36 g of aluminum nitrate nonahydrate [$Al(NO_3)_3 \cdot 9H_2O$] were dissolved to prepare an aqueous solution (solution A). On the other hand, 87.44 g of sodium carbonate decahydrate [$Na_2CO_3 \cdot 10H_2O$] was dissolved in 870 ml of pure water to prepare an aqueous solution (solution B). A flask containing 800 ml of water was prepared, and with stirring water in the flask at room temperature, the solution A and the solution B were dropwise added to the water at the same rates. After the resulting slurry was stirred for 150 minutes, the precipitate in the slurry was subjected to vacuum filtration and sufficiently washed with distilled water. Thereafter, the recovered precipitate was dried for 12 hours in a dryer adjusted to 80° C., and then calcined for 3 hours in an electric furnace adjusted to 350° C. in the atmosphere, to obtain an oxide. The oxide was subjected to tablet-making molding and pulverized, followed by collecting 10 ml of the pulverizate. The pulverizate was charged in a small reaction tube and subjected to reduction treatment with a mixed gas of $H_2/N_2$ (1/9) under the conditions of GHSV of 6000 ($hr^{-1}$) and 350° C. to obtain a catalyst 1 (mass % of element: Cu 40%, Zn 36%, Al 3%, atomic ratio of Zn to Cu: 0.87).

Example 2

Preparation of Catalyst

In 700 ml of pure water, 23.14 g of copper nitrate trihydrate [$Cu(NO_3)_2 \cdot 3H_2O$], 40.21 g of zinc nitrate hexahydrate [$Zn(NO_3)_2 \cdot 6H_2O$], 1.93 g of iron nitrate nonahydrate [$Fe(NO_3)_3 \cdot 9H_2O$] and 7.36 g of aluminum nitrate nonahydrate [$Al(NO_3)_3 \cdot 9H_2O$] were dissolved to prepare an aqueous solution (solution A). On the other hand, 88.03 g of sodium carbonate decahydrate [$Na_2CO_3 \cdot 10H_2O$] was dissolved in 880 ml of pure water to prepare an aqueous solution (solution B). A flask containing 800 ml of water was prepared, and with stirring water in the flask at room temperature, the solution A and the solution B were dropwise added to the water at the same rates. After the resulting slurry was stirred for 150 minutes, the precipitate in the slurry was subjected to vacuum filtration and sufficiently washed with distilled water. Thereafter, the recovered precipitate was dried for 12 hours in a dryer adjusted to 80° C., and then calcined for 3 hours in an electric furnace adjusted to 350° C. in the atmosphere, to obtain an oxide. The oxide was subjected to tablet-making molding and pulverized, followed by collecting 10 ml of the pulverizate. The pulverizate was charged in a small reaction tube and subjected to reduction treatment with a mixed gas of $H_2/N_2$ (1/9) under the conditions of GHSV of 6000 ($hr^{-1}$) and 350° C. to obtain a catalyst 2 (mass % of element: Cu 30%, Zn 44%, Al 3%, Fe 1%, atomic ratio of Zn to Cu: 1.42).

Example 3

In a quartz glass reactor having a diameter of 3 cm and a length of 40 cm, 1.0 g of the catalyst 1 and 1.0 g of β zeolite (available from Catalysts & Chemicals Industries Co., Ltd., having been compression molded at 20 MPa and then classified as that of 250 to 500μ) were charged, then they were dried at 350° C. for 1 hour in a stream of nitrogen at 30 ml/min, and thereafter they were subjected to reduction treatment at 350° C. for 1 hour in a stream of hydrogen at 11 ml/min. Still in a stream of hydrogen, the temperature was lowered to 160° C., then a mixed liquid of benzene/acetone (5/1 by mol) was passed through the reactor at a rate of 1.2 ml/min, and the exit was cooled to capture the product. The product after 3 hours from the beginning of the reaction was analyzed by gas chromatography, and as a result, concentrations of the components other than benzene and water were: acetone 0.1%, cumene 72.0%, m-diisopropylbenzene 19.9% and p-diisopropylbenzene 8.0%, in terms of weight ratio.

Example 4

Reaction was carried out in the same manner as in Example 3, except that the catalyst 2 was used instead of the catalyst 1. The product after 3 hours from the beginning of the reaction was analyzed by gas chromatography, and as a result, concentrations of the components other than benzene and water were: acetone 0%, cumene 88.9%, m-diisopropylbenzene 7.9% and p-diisopropylbenzene 3.1%, in terms of weight ratio.

Comparative Example 1

Reaction was carried out in the same manner as in Example 3, except that copper chromite (available from Sud-Chemie AG, product name: G99b, mass % of element: Cu 35%, Cr 31%, Ba 2%, Mn 3%, atomic ratio of Zn to Cu: 0) was used instead of the catalyst 1. The product after 3 hours from the beginning of the reaction was analyzed by gas chromatography, and as a result, concentrations of the components other than benzene and water were: acetone 8.4%, cumene 56.7%, m-diisopropylbenzene 23.6% and p-diisopropylbenzene 11.1%, in terms of weight ratio.

Comparative Example 2

Reaction was carried out in the same manner as in Example 3, except that a catalyst using copper aluminate as a base (available from Sud-Chemie AG, product name: T4489, mass % of element: Cu 39%, Al 16%, Zn 6%, Mn 7%, atomic ratio of Zn to Cu: 0.15) was used instead of the catalyst 1. The product after 3 hours from the beginning of the reaction was analyzed by gas chromatography, and as a result, concentrations of the components other than benzene and water were: acetone 8.8%, cumene 55.0%, m-diisopropylbenzene 22.1% and p-diisopropylbenzene 10.7%, in terms of weight ratio.

Example 5

In a quartz glass reactor having a diameter of 3 cm and a length of 40 cm, 1.0 g of the catalyst 2 and 1.0 g of MCM-22 zeolite (obtained by compression molding a catalyst prepared in accordance with VERIFIED SYNTHESES OF ZEOLITIC MATERIALS Second Revised Edition 2001, p. 225, at 20 MPa and then classifying it as that of 250 to 500μ) were charged, then they were dried at 350° C. for 1 hour in a stream of nitrogen at 30 ml/min, and thereafter they were subjected to reduction treatment at 200° C. for 3 hours in a stream of hydrogen at 10 ml/min. Thereafter, the temperature was lowered to 150° C. in a stream of hydrogen at 3 ml/min, then a mixed liquid of benzene/acetone (3/1 by mol) was passed through the reactor at a rate of 1.2 ml/min, and the exit was cooled to capture the product. In addition, capture of gas was also carried out though it was not carried out in the above examples and comparative examples. The product after 3 hours from the beginning of the reaction was analyzed by gas chromatography (column for gas phase analysis: PLOT FUSED SILICA 50M×0.32MM ID COATING AL203/NA2SO4 DF=5UM, manufactured by VARIAN Inc., column for liquid phase analysis: ZB-WAX, manufactured by Phenomenex Inc.), and as a result, cumene, m-diisopropylbenzene and p-diisopropylbenzene, which were values, were obtained in high yields, as shown in Table 1.

Example 6

Reaction was carried out under the same conditions as in Example 5, except that a commercially available copper-zinc catalyst (available from Sud-Chemie AG, product name: Shift Max 210, mass % of element: Cu 32 to 35%, Zn 35 to 40%, Al 4 to 7%, atomic ratio of Zn to Cu: 1.00 to 1.20) was used instead of the catalyst 2, and D zeolite (available from Catalysts & Chemicals Industries Co., Ltd., having been compression molded at 20 MPa and then classified as that of 250 to 500μ) was used instead of MCM-22. The product after 3 hours from the beginning of the reaction was analyzed by gas chromatography, and as a result, cumene, m-diisopropylbenzene and p-diisopropylbenzene, which were values, were obtained in high yields, as shown in Table 1.

Example 7

Reaction was carried out under the same conditions as in Example 5, except that a commercially available copper-zinc catalyst (available from Sud-Chemie AG, product name: Shift Max 210, mass % of element: Cu 32 to 35%, Zn 35 to 40%, Al 4 to 7%, atomic ratio of Zn to Cu: 1.00 to 1.20) was used instead of the catalyst 2. The product after 3 hours from the beginning of the reaction was analyzed by gas chromatography, and as a result, cumene, m-diisopropylbenzene and p-diisopropylbenzene, which were values, were obtained in high yields, as shown in Table 1.

Example 8

Using a fixed bed reaction device equipped with a high-pressure feed pump, a high-pressure hydrogen mass flow, a high-pressure nitrogen mass flow, an electric furnace, a reactor having a catalyst charge part, and a backpressure valve, pressurized liquid phase flow reaction by a down flow was carried out.

In a SUS 316 reactor having an inner diameter of 1 cm, 1.0 g of a powder (having been classified as that of 250 to 500μ) of a copper-zinc catalyst (available from Sud-Chemie AG, product name: Shift Max 210, mass % of element: Cu 32 to 35%, Zn 35 to 40%, Al 6 to 7%, atomic ratio of Zn to Cu: 1.0 to 1.2) was first charged from the exit side of the reactor as a catalyst layer on the upstream side. After quartz wool was packed, 3.0 g of the aforesaid MCM-22 (obtained by compression molding a catalyst prepared in accordance with VERIFIED SYNTHESES OF ZEOLITIC MATERIALS Second Revised Edition 2001, p. 225, at 20 MPa and then classifying it as that of 250 to 500 μ, Si/Al molar ratio: 20) was charged as a catalyst layer on the downstream side.

The reactor was pressurized to 3 MPa with hydrogen, and then reduction treatment was carried out at 200° C. for 3 hours in a stream of hydrogen at 12.5 ml/min given from the entrance side of the reactor. Still in a stream of hydrogen at 12.5 ml/min, the temperature was lowered to 175° C., and a mixed liquid of benzene/acetone (3/1 by mol) was fed from the entrance side of the reactor and passed through the reactor at a rate of 2.50 g/hr.

By the use of the high-pressure nitrogen mass flow, nitrogen was introduced at 200 ml/min into the middle part between the reactor exit and the backpressure valve. In the line after the backpressure valve, a switching valve was installed, then a reaction gas was introduced into an injection of gas chromatography through a sampling tube of 0.2 ml, and the product was determined by gas chromatography analysis.

The reaction result is set forth in Table 1. By separating the copper-zinc catalyst and MCM-22 from each other, side production of propane was decreased though acetone remained, and cumene was obtained highly selectively.

Comparative Example 3

Reaction was carried out in the same manner as in Example 6, except that copper chromite (available from Sud-Chemie AG, product name: G99b, mass % of element: Cu 35%, Cr 31%, Ba 2%, Mn 3%, atomic ratio of Zn to Cu: 0) was used instead of Shift Max 210. The product after 3 hours from the beginning of the reaction was analyzed by gas chromatography, and as a result, selectivities of cumene, m-diisopropylbenzene and p-diisopropylbenzene, which were values, were low, and side production of hydrocarbons derived from acetone was extremely large, as shown in Table 1.

Comparative Example 4

Reaction was carried out in the same manner as in Example 6, except that a copper-alumina catalyst (available from Nikki Chemical Co., Ltd., product name: N242, mass % of element: Cu 40%, Al: 18%) was used instead of Shift Max 210. The product after 3 hours from the beginning of the reaction was analyzed by gas chromatography, and as a result, conversion of acetone was extremely low, and side production of impurities was large, as shown in Table 1. Therefore, yields of cumene, m-diisopropylbenzene and p-diisopropylbenzene, which were values, were low.

TABLE 1

|  | Ex. 5 | Ex. 6 | Ex. 7 | Ex. 8 | Comp. Ex. 3 | Comp. Ex. 4 |
|---|---|---|---|---|---|---|
| Catalyst |  |  |  |  |  |  |
| Reduction catalyst | Catalyst 2 | Cu—Zn | Cu—Zn | Cu—Zn | Cu—Cr | Cu—Al |
| Acid Catalyst | MCM-22 | β | MCM-22 | MCM-22 | β | β |

TABLE 1-continued

|  | Ex. 5 | Ex. 6 | Ex. 7 | Ex. 8 | Comp. Ex. 3 | Comp. Ex. 4 |
|---|---|---|---|---|---|---|
| Reaction conditions | | | | | | |
| Reaction temperature (° C.) | 150 | 150 | 150 | 175 | 150 | 150 |
| Benzene/acetone molar ratio | 3.0 | 3.0 | 3.0 | 3.0 | 3.0 | 3.0 |
| Hydrogen/acetone molar ratio | 2.0 | 2.0 | 2.0 | 4.0 | 2.0 | 2.0 |
| WHSV (hr$^{-1}$) | 0.5 | 0.5 | 0.5 | 0.6 | 0.5 | 0.5 |
| Pressure (MPa) | 0 | 0 | 0 | 3.0 | 0 | 0 |
| Reaction result | | | | | | |
| Conversion of acetone (%) | 99.7 | 99.0 | 100.0 | 97.0 | 95.0 | 56.3 |
| Selectivity/acetone base (%) | | | | | | |
| Propane + C4 hydrocarbon | 2.8 | 7.6 | 0.5 | 1.3 | 25.1 | 8.6 |
| Diisopropyl ether | 0.0 | 0.0 | 0.0 | 0.4 | 1.4 | 0.0 |
| Isopropanol | 0.0 | 0.0 | 0.0 | 0.0 | 0.0 | 0.0 |
| Cumene | 70.0 | 41.1 | 66.2 | 81.6 | 33.2 | 35.2 |
| Diisopropylbenzene | 23.4 | 47.3 | 27.3 | 16.7 | 31.4 | 38.2 |
| High-boiling substance | 3.8 | 4.0 | 6.0 | 0.0 | 8.9 | 18.2 |
| Selectivity of values* (%) | 93.4 | 88.4 | 93.5 | 98.3 | 64.6 | 73.4 |
| Selectivity of impurities** (%) | 6.6 | 11.6 | 6.5 | 1.7 | 35.4 | 26.6 |

*Values: cumene + diisopropylbenzene
**Impurities: propane + C4 hydrocarbon + diisopropyl ether + high-boiling substance

INDUSTRIAL APPLICABILITY

The present invention provides a process in which a ketone such as acetone, an aromatic compound such as benzene and hydrogen are used as starting materials to obtain the corresponding alkylated aromatic compound such as cumene in a single reaction step in a higher yield.

This process is applicable to a process for industrially producing phenol, etc.

The invention claimed is:

1. A process for preparing an alkylated aromatic compound, comprising reacting an aromatic compound with a ketone and hydrogen in the presence of a solid acid substance and a catalyst composition containing Cu and Zn in a ratio of Zn to Cu ranging from 0.70 to 1.60 (atomic ratio).

2. The process for preparing the alkylated aromatic compound as claimed in claim 1, wherein the aromatic compound is benzene, and the ketone is acetone.

3. The process for preparing the alkylated aromatic compound as claimed in claim 1, wherein the solid acid substance is a zeolite compound.

4. The process for preparing the alkylated aromatic compound as claimed in claim 3, wherein the zeolite compound is a zeolite compound having a 10- to 16-membered oxygen ring.

5. The process for preparing the alkylated aromatic compound as claimed in claim 4, wherein the zeolite compound is selected from the group consisting of zeolite β, zeolite Y, ZSM-12, mordenite, MCM-22, MCM-56 and ZSM-5.

6. The process for preparing the alkylated aromatic compound as claimed in claim 5, wherein the zeolite compound is MCM-22, MCM-56 or ZSM-5.

7. A process for preparing phenol, comprising the following steps of:
    (a) a step of oxidizing cumene to convert it into cumene hydroperoxide,
    (b) a step of acid decomposing the cumene hydroperoxide to synthesize phenol and acetone,
    (c) a step of reacting the acetone formed in the step (b) with benzene to synthesize cumene, and
    (d) a step of recycling the cumene obtained in the step (c) to the step (a),
    wherein the step (c) is carried out in accordance with the process for preparing the alkylated aromatic compound of claim 1.

* * * * *